US007998735B2

(12) United States Patent
Morrison et al.

(10) Patent No.: US 7,998,735 B2
(45) Date of Patent: Aug. 16, 2011

(54) VASCULARIZED TISSUE GRAFT

(75) Inventors: Wayne A Morrison, Hawthorn (AU);
Aurora Messina, Eltham North (AU);
Kenneth R Knight, Mount Waverly (AU); Anthony J Penington, Hawthorn (AU)

(73) Assignee: Victorian Tissue Engineering Centre Pty. Ltd., Fitzroy Victoria (AU)

( * ) Notice: Subject to any disclaimer, the term of this patent is extended or adjusted under 35 U.S.C. 154(b) by 415 days.

(21) Appl. No.: 10/888,436

(22) Filed: Jul. 8, 2004

(65) Prior Publication Data

US 2005/0056291 A1 Mar. 17, 2005

Related U.S. Application Data

(63) Continuation-in-part of application No. 10/362,243, filed as application No. PCT/AU01/01031 on Aug. 21, 2001, now abandoned.

(60) Provisional application No. 60/252,497, filed on Nov. 22, 2000.

(30) Foreign Application Priority Data

Aug. 21, 2000 (AU) ............................ PQ9553
Jul. 8, 2003 (AU) .............................. 2003903513

(51) Int. Cl.
*C12N 5/00* (2006.01)
(52) U.S. Cl. ...................... 435/325; 435/395; 435/382
(58) Field of Classification Search .................... None
See application file for complete search history.

(56) References Cited

U.S. PATENT DOCUMENTS

| 4,414,980 | A |   | 11/1983 | Mott |  |
|---|---|---|---|---|---|
| 4,963,489 | A | * | 10/1990 | Naughton et al. | ............. 435/1.1 |
| 5,192,321 | A |   | 3/1993 | Strokon |  |
| 5,510,254 | A |   | 4/1996 | Naughton et al. |  |
| 5,811,266 | A |   | 9/1998 | Newgard |  |
| 5,916,554 | A |   | 6/1999 | Dionne et al. |  |
| 5,919,449 | A |   | 7/1999 | Dinsmore |  |

FOREIGN PATENT DOCUMENTS

| JP | 07508663 T2 | 9/1995 |
|---|---|---|
| JP | 08500033 T2 | 1/1996 |
| WO | WO 93/08850 | 5/1993 |
| WO | WO 9403154 A1 | 2/1994 |
| WO | WO 96/18424 | 6/1996 |
| WO | WO 96/40002 | 12/1996 |

OTHER PUBLICATIONS

Eppley BL et al. 1990. Experimental effects of graft revascularization and consistency on cervicofacial fat transplant survival. J Oral Maxillofacial Surg 48: 54-62.*
Antia NH et al. 1971. Transfer of an abdominal dermo-fat graft by direct anastomosis of blood vessels. Br J Plast Surg 24:15-9.*
Wells JH et al. 1977. Correction of severe hemifacial atrophy with a free dermis-flat from the lower abdomen. Plast Reconstr Surg 59:223-30.*
Tosh D et al. 2002. Conversion of pancreatic cells to hepatocytes. Biochem Soc Trans 30: 51-54.*
Eppley BL et al. 1992. The epigastric fat transfer: An alternative free flap model in the rat. Ann Plast Surg 29: 293-296.*
Khouri et al. Tissue generation with growth factors. *Surgery* 1993, p. 374-380, 114: 2.
Erol et al. New Capillary Bed Formation with a Surgically Constructed Arteriovenous Fistula. *Plast. Reconstr. Surg.* Jul. 1980, 109-115.
Tanaka, Y., Tajima, S., Tsutsumi, A., Akamatsu, J., and Ohba, S., "New Matrix Flap Prefabricated by Arteriovenous Shunting and Artificial Skin Dermis in Rats: II," J.Jpn.P.R.S.; 16: 679-686. (1996).
Germain, et al., "[*Prefabricated free transplants. Experimentation*] Les Transplants libres prefabriques experimentation," Ann Oto-Larying 106: 351-353. (1989).
Lee, et al., "De novo induction of island capsule flap by using two silastic sheets: part 1. generation," Plast Reconstr. Surg., 104:1023-1028. (1999).
Machens, et al., "Genetically modified fibroblasts induce angiogenesis in the rat epigastric island flap," Biol. Matrices Tissue Reconstr., Editors: Stark et al., Publisher: Springer, Berlin, Germany, pp. 53-59. (1998).
Vijanen, et al., "Producing vascularized bone by heterotopic bone induction and guided tissue regeneration: a silicone membrane-isolated latissimus dorsi island flap in a rat model," J. Reconstr. Microsurg., vol. 13: 207-214.
Vogelin, et al., "Heterotopic and orthotopic bone formation with a vascularized periosteal flap, a matrix and rh-bmp-2 (bone morphogenetic protein) in the rat model," Mund Kiefer Gesichtshir., Suppl., Medline Abstract PMID: 11094515, vol. 2: S454-458. (2000).
Sembeil R et al. 2004 "Prolonged Survival of mouse skin allografts after transplantation of fetal liver cells transduced with hIL-10 gene." *Transplant Immunol* 13:1-8.
Li W-C et al. 2005 "The molecular basis of transdifferentiation." *J Cell Mol Med* 9:569-582.
Tanaka Y et al. 2000 Generation of an autologous tissue (matrix) flap by combining an arteriovenous shunt loop with artificial skin in rats: preliminary report *B J Plast Surg* 53:51-57.
Kurtz A et al. 1997 "Expression of a binding protein for FGF is associated with epithelial development and skin carcinogenesis." *Oncogene* 14:2671-2681.
Hirase Y et al. 1993 "Transplantation of long-term cryopreserved allocutaneous tissue by skin graft or microsurgical anastomosis: experimental studies in the rat." *Plast Reconstr Surg* 91:492-501.
Sullivan SJ et al. 1991 Biohybrid artificial pancreas: long-term implantation studies in diabetic, pancreatectomized dogs. *Science* 252:718-721.
Bonini P. et al. 2001 Neurotrophins and neurotrophin receptors mRNAs expression in pancreatic islets and insulinoma cell lines. *J Pancreas* 2:105-111.

(Continued)

*Primary Examiner* — Lora E Barnhart
(74) *Attorney, Agent, or Firm* — Knobbe Martens Olson & Bear LLP (57) ABSTRACT

Improved methods for tissue engineering including tissue transplantation, augmentation and regeneration are described. These methods utilize a support matrix in the generation of an anatomical construct that includes donor vascularized tissue. The support matrix may be devised such that it has size and shape adapted to simulate the dimensions of tissue to be transplanted, augmented and/or repaired.

4 Claims, 4 Drawing Sheets

OTHER PUBLICATIONS

Merriam-Webster Medical Dictionary entry for "seed." http://www.nlm.nih.gov/medlinplus/mplusdictionary.html, accessed Aug. 16, 2006 1 page.

Bonini, P. et al. 2001 "Neurotrophins and neurotropin receptors mRNAs expression in pancreatic islets and insulinoma cell lines" *J Pancreas* 2:105-111.

Hirase, Y. et al. 1993 "Transplantation of long-term cryopreserved allocutaneous tissue by skin graft or microsurgical anastomosis: experimental studies in the rat" *Plast Reconstr Surg* 91:492-501.

Kurtz, A. et al. 1997 "Expression of a binding protein for FGF is associated with epithelial development and skin carcinogenesis" *Oncogene* 14:2671-2681.

Li, W-C et al. 2005 "The molecular basis of transdifferentiation" *J Cell Mol Med* 9:569-582.

Sembeil, R. et al. 2004 "Prolonged survival of mouse skin allografts after transplantation of fetal liver cells transduced with hIL-10 gene" *Transplant Immunol* 13:1-8.

Sullivan, SJ et al. 1991 "Biohybrid artificial pancreas: long-term implantation studies in diabetic, pancreatectomized dogs" *Science* 252:718-721.

Tanaka, Y. et al. 1996 New matrix flap prefabricated by arteriovenous shunting and artificial skin dermis in rats: II. Effect of interpositional vein or artery grafts and bFGF on new tissue generation. *J Jpn Plast Reconst Surg* 16:679-686.

Tanaka, Y. et al. 2000 "Generation of an autologous tissue (matrix) flap by combining an arteriovenous shunt loop with artificial skin in rats: preliminary report" *Br J Plast Surg* 53:51-57.

Albrektsson, T.A. 1985 "Molded vascularized osteoneogenesis: A preliminary study in rabbits" *Plastic and Reconstr Surg* 76:857-858.

Mizumoto, S. et al. 1992 "Pre-formed vascularized bone grafts using polyethylene chambers" *J Reconstr Microsurg* 8:325-333.

Picha, G.J. et al. 1991 "Microvascular A-V shunts and the growth of autologous tissue flaps in Millipore chambers" *Plastic and Reconstr Surg* 87:509-517.

Antia, NH et al. 1971 "Transfer of an abdominal dermo-fat graft by direct anastomosis of blood vessels" *Br J Plast Surg* 24:15-19.

Eppley, BL et al. 1990 "Experimental effects of graft revascularization and consistency on cerivcofacial fat transplant survival" *J Oral Maxilofacial Surg* 48:54-62.

Wells, JH et al. 1977 "Correction of severe hemifacial atrophy with a free dermis-flat from the lower abdomen" *Plast Reconstr Surg* 59:223-230.

Office Action in Japanese Application No. 2002-520835, dispatched Jun. 1, 2011.

* cited by examiner

VASCULARIZED TISSUE GRAFT

RELATED APPLICATIONS

The present application is a continuation-in-part of U.S. application Ser. No. 10/362,243, filed Sep. 22, 2003, which is the U.S. national phase under 35 U.S.C. §371 of International Application No. PCT/AU01/01031, filed Aug. 21, 2001, which claims priority under 35 U.S.C. §119(e) to U.S. Provisional Application No. 60/252,497, filed Nov. 22, 2000.

BACKGROUND OF THE INVENTION

1. Field of the Invention

The present invention relates generally to improved methods for tissue engineering including tissue transplantation, augmentation and regeneration. More particularly, the present invention provides a method for the generation of donor vascularized tissue suitable for use in tissue transplantation, augmentation and/or repair. The present invention further enables the use of a support matrix in the generation of an anatomical construct comprising the donor vascular tissue. The support matrix may be devised such that it has dimensions of a size and shape adapted to simulate those of tissue to be transplanted, augmented and/or repaired. In addition to its use in tissue repair, the methods and support matrix of the present invention may also find application as a means for delivering a desirable gene product to a subject. The method and support matrix of the present invention is conveniently be made available in the form of a kit, for use generally in the field of tissue engineering.

2. Description of the Related Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Tissue engineering utilizing homologous starting material offers the prospect of replacing missing or non-functioning body parts with newly created, living tissue. It has the potential to minimize loss of tissue and resultant pain from the donor site experienced in conventional reconstructive surgery or to recreate specialized tissue for which there is no donor site, while obviating the long-term immunosuppression required for heterologous transplantation.

It combines the techniques of tissue culture, the creation of bio-compatible materials and the manipulation of angiogenesis in order to create new, vascularized tissue to replace damaged tissue or tissue which is congenitally absent.

One of the major challenges faced in tissue engineering is to create differentiated tissue of the appropriate size and shape. Tissue created without a functional vasculature is strictly limited in size by the constraints of oxygen diffusion; if the tissue is too large it will become necrotic before the host has time to create a new blood vessel supply. Thus there are many advantages in creating new tissue containing a functional vasculature. Additionally, as the new tissue may need to be produced at a site on the body remote from the defect, or on an immuno-suppressed carrier animal or in vitro with an extra-corporeal circulation, the blood supply for the new tissue must be defined, so that it can be brought with the tissue intact to the site of reconstruction.

The creation of skin flaps, a living composite of skin and its underlying fat, is a common technique used to repair tissue defects in reconstructive surgery. Because these flaps must retain their blood supply to remain viable after transplantation, the origin of the flaps is limited to those areas where there is an anatomically recognized blood vessel source. In order to overcome this limitation, skin flaps can be "prefabricated" by implanting short segments of blood vessels into a desired site, and utilizing the resultant angiogenesis to vascularize a flap of the desired size and composition. Subsequently this vascularized flap can be transferred by microsurgery to the region of interest. This technique is, however, limited by the availability of donor tissue, and the disfigurement that results at the donor site.

In an extension to this technique, Erol and Spira, *Surgery* 66: 109-115, 1980 demonstrated that the creation of an anastomosed arteriovenous (AV) loop beneath a skin graft could produce a vascularized skin "flap".

However, while the generation of vascularized skin using an AV loop has been demonstrated, the production of other vascularized tissues suitable for grafting remains elusive. Vascularized adipose tissue, for example, is often demanded in reconstructive procedures; however, donor mature adipose tissue is extremely fragile, and will rapidly become necrotic if not immediately reconnected to a functional blood supply. Furthermore, the use of conventional autologous transplantation techniques involves "robbing Peter to pay Paul", producing disfigurement at the donor site. The ability to produce new tissue with a defined vasculature would overcome this major shortcoming.

Khouri et al., *Surgery* 114: 374-380, 1993 and Tanaka et al., *Jpn. PRS* 16: 679-686, 1996 have demonstrated that an arteriovenous loop could intrinsically generate new, vascularized tissue when it was lifted from the body, sandwiched between sheets of collagenous matrix and isolated from the surrounding tissue within a plastic chamber. In the model described by Khouri et al., 1993, supra the generation of new tissue relied on the addition of recombinant BB-homodimer of Platelet-Derived Growth Factor (BB-PDGF), and even with this supplement the tissue was labile, peaking in volume at 15 days and subsiding by 30 days. Similarly, tissue growth in Tanaka's model, where the chamber was supplemented with β-Fibroblast Growth Factor (β-FGF or FGF-2), continued to increase in volume, peaking at two weeks but returned to the levels of the unsupplemented control chambers after four weeks. This AV loop model is not generally known in the field of tissue engineering.

International Patent Application No. PCT/AU01/01031 (International Patent Publication No. WO 02/15914) describes inter alia the use of an AV loop in a fabricated chamber which is implanted into a subject. Tissue was found to successfully grow around the AV loop in a shape dependent on the constraints of the chamber.

Despite the success of the methodology and chamber described in International Patent Publication No. WO 02/15914, there is a need to further improve the growth of tissue around a functional circulatory system.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention provides an improved method for generating vascularized tissue for use in tissue engineering including tissue transplantation, augmentation and regeneration. In essence, the method comprises growing vascularized tissue around a functional circulatory system in the form of a vascular pedicle which comprises tissue or an extract or component thereof associated therewith within a support matrix. Additional cellular material or components thereof or recombinant or synthetic forms of these components may also be added to the support matrix. The support matrix comprising the tissue and circulatory system is inserted into a body cavity or other suitable location such as a subcutaneous site in a host. After time and conditions sufficient for vascularized tissue to grow around the circulatory system, the support matrix is removed and the vascularized tissue implanted into the desired location within or on the same host or a compatible recipient.

One aspect of the present invention provides, therefore, a method for generating vascularized tissue suitable for transplantation into a recipient. Another aspect of the present invention is directed to a support matrix in and/or around which vascularized tissue can grow. Still another aspect of the present invention provides a method of tissue replacement and/or regeneration comprising generating replacement vascularized tissue within a recipient and transplanting this vascularized tissue to a desired location within or on the recipient or another compatible recipient. Yet another aspect provides a kit for use in generating vascularized tissue, optionally with instructions for use.

In a preferred embodiment, the support matrix is in the form of a fabricated chamber having in one embodiment a defined internal and/or external shape. In use, the fabricated chamber comprises an AV loop or shunt or other suitable circulatory system in the form of a vascular pedicle. The vascular pedicle also comprises additional tissue such as fat or adipose tissue or tissue comprising myoblasts, fibroblasts, pre-adipocytes and adipocytes, cardiomyocytes, keratinocytes, endothelial cells, smooth muscle cells, chondrocytes, pericytes, bone marrow-derived stromal precursor cells, embryonic, mesenchymal or haematopoietic stem cells, Schwann cells and other cells of the peripheral and central nervous system, olfactory cells, hepatocytes and other liver cells, mesangial and other kidney cells, pancreatic islet β-cells and ductal cells, thyroid cells and cells of other endocrine organs. Alternatively, or in addition, extracts of the fat or adipose tissue or other tissue or recombinant or synthetic forms of components of fat or adipose tissue or other tissue are associated or impregnated into the vascular pedicle. Donor tissue then grows around the circulatory system and its fat or adipose or other tissue or their components.

The method of the present invention results in the generation of vascularized tissue of a particular size and shape within or on the support matrix. The size and shape depends on the dimensions of the support matrix. This vascularized tissue may be used as a graft in transplantation and/or reconstructive surgery as well as in organ or tissue augmentation or regeneration.

In a preferred embodiment, the vascular pedicle comprises attached tissue prior to being associated with the support matrix. The attached tissue is preferably vascularized fat or adipose tissue although the present invention extends to a range of tissues as indicated above.

In circumstances where, for example, stem cell expansion, development and differentiation may form the basis for the generation of new tissue de novo, an expandable microenvironment comprising an inert support and/or one or more additional extracellular matrix components may also be desirable. Hence, it may be desirable for one or more of a growth factor, drug, antibody or other chemical to be added or associated to the support matrix in or on which the vascularized new tissue is being generated.

The present invention further provides a vascularized tissue comprising differentiated tissue with a vascular supply suitable for use as a graft in tissue transplantation and/or tissue repair or augmentation or tissue regeneration.

A further aspect of the present invention contemplates a method of repairing a tissue deficit comprising the step of implanting a solid matrix comprising a vascular pedicle comprising a functional circulatory system and tissue associated or mounted to the vascular pedicle into a recipient, permitting tissue to grow around the vascular pedicle for a time to achieve the desired size, vascularity and degree of differentiation, transferring the generated tissue with or without the support matrix in the recipient or a compatible recipient and then microsurgically anastomosing the circulatory system to a local artery and vein.

The ability to repair a tissue deficit and/or augment inappropriately depleted tissue using the method of the present invention provides the further possibility of facilitating the delivery of one or more desirable gene product(s) to a subject. Cells and/or developing tissue within or on the support matrix may be transformed with an appropriate genetic construct comprising the desired gene prior to being transplanted into the recipient.

The methods, support matrix and vascularized tissue of the present invention may also be used to create an entire system which may be connected to external apparatus such as, for example, a dialysis filter.

Accordingly, the present invention further contemplates a model system for vascularized tissue, comprising a support matrix containing the vascular pedicle and additional tissue or extract or component thereof and optionally an extracellular matrix, operably connected to an extra-corporeal circulation apparatus and renal dialysis filter.

Suitable additional extracellular matrix components include, for example, reconstituted basement membrane preparations, polylactic-polyglycolic acid (PLGA) variants, fibrin or plasma glue and native collagen.

BRIEF DESCRIPTION OF THE DRAWINGS

FIG. 1 is a diagrammatic representation illustrating how the femoral artery and vein are anastomosed micro-surgically to a vein graft of similar diameter to form a loop (shunt). The AV loop is placed as shown in a plastic chamber (made of polycarbonate or poly-L-lactic acid, etc) comprising additional tissue such as fat or adipose tissue. The lid is then secured, and the chamber optionally filled with an extracellular matrix with or without added cells or growth factors. The chamber is anchored in position relative to the surrounding tissue by means of stay sutures through external holes.

FIG. 3 is a diagrammatic representation depicting an example of the thin-walled chamber used for the pedicle model. In this case, an artery and a vein are ligated distally and placed adjacent to each other. Microscopic connections between the artery and vein become established, and form an AV loop in a similar manner to that shown in FIGS. 1 and 2.

DETAILED DESCRIPTION OF THE PREFERRED EMBODIMENTS

The present invention is predicated in part on the elucidation of an improved means of generating vascularized tissue for use inter alia in transplantation and/or reconstructive surgery, for tissue repair, augmentation and/or regeneration and/ or to deliver a desirable gene or genes to an in vivo site. The present invention provides, therefore, a method for tissue engineering as well as components useful for same.

Accordingly, one aspect of the present invention provides a method of generating donor vascularized tissue suitable for transplantation into a recipient, said method comprising creating a vascular pedicle comprising a functional circulatory system and having tissue or tissue extract or a component thereof impregnated, attached or otherwise associated with the vascular pedicle; associating the vascular pedicle within and/or on a support matrix; optionally seeding the support matrix with isolated cells or pieces of tissue; implanting the support matrix containing the vascular pedicle into a recipient at a site where the functional circulatory system is anastomosized to a local artery or vein; and leaving the support matrix at the implantation site for a period sufficient to allow the growth of vascularized new tissue.

In a preferred embodiment, the vascular pedicle comprises attached fat or other adipose tissue or tissue comprising myoblasts, fibroblasts, pre-adipocytes and adipocytes, cardiomyocytes, keratinocytes, endothelial cells, smooth muscle cells, chondrocytes, pericytes, bone marrow-derived stromal precursor cells, embryonic, mesenchymal or haematopoietic stem cells, Schwann cells and other cells of the peripheral and central nervous system, olfactory cells, hepatocytes and other liver cells, mesangial and other kidney cells, pancreatic islet β-cells and ductal cells, thyroid cells and cells of other endocrine organs. The presence of the attached tissue on the vascular pedicle further facilitates the growth of new fat tissue in or around the support matrix. In an alternative embodiment, tissue extract or a recombinant, synthetic or purified component of the tissue is associated with the vascular pedicle.

The preferred support matrix is in the form of a fabricated chamber having an internal and/or external portion of a defined size and/or shape. In one embodiment, the vascular pedicle comprising the functional circulatory system and the additional fat or adipose tissue or other tissue or component is enclosed within the fabricated chamber. In another embodiment, the vascular pedicle comprising the functional circulatory system and the additional fat or adipose tissue or other tissue or component is associated within or around one or more layers of a support matrix. The support matrix such as the fabricated chamber may be rigid, semi-rigid, flexible or collapsible.

The term "vascular pedicle" extends to and encompasses a pedicle on which there remain cells that constitute an attached tissue prior to the pedicle being introduced into the fabricated chamber or associated with the support matrix.

The optional step of adding isolated cells or pieces of tissue to the support matrix is useful in influencing the type of donor vascularized tissue that is produced. The isolated cells or pieces of tissue includes, as mentioned above, the one or more cells that may remain attached to the vascular pedicle prior to its being partially or totally enclosed within the fabricated chamber.

In a particularly preferred embodiment, the present invention provides a method of generating donor vascularized tissue suitable for transplantation into a recipient comprising creating a vascular pedicle comprising an AV loop or shunt having tissue or tissue extract or a component thereof impregnated, attached or otherwise associated with the vascular pedicle; associating the vascular pedicle within and/or on a fabricated chamber; optionally seeding the fabricated chamber with isolated cells or pieces of tissue; implanting the fabricated chamber containing the vascular pedicle into a recipient at a site where the AV loop or shunt is anastomosized to a local vein or artery and leaving the fabricated chamber at the implantation site for a period sufficient to allow the growth of new vascularized tissue.

In another embodiment, the method comprises the additional step of surrounding the vascular pedicle with added extracellular matrix and/or a mechanical support and/or adding one or more growth factors, drugs, antibodies or other chemicals to the chamber.

Preferably, the support matrix is left in the implantation site for at least two weeks, preferably at least four weeks and even more preferably, at least six weeks. Examples include for at least 3, 4, 5, 6 7, 8, 9 or 10 weeks. More particularly, the support matrix is left at the implantation site for about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 days.

Although it is preferable for the support matrix to be implanted in a suitable recipient in order to grow tissue, it may also be maintained in vitro in the presence of suitable components in order for tissue to grow. For in vivo use, the support matrix is implanted in the recipient in a body cavity or beneath the skin. When suitably protected, the support matrix may also be maintained outside the body.

For the purposes of this specification, the term "recipient" is taken to mean an animal, especially a mammal and most especially a human, in which the donor vascularized tissue is created. Generally, the recipient in which the vascularized tissue is grown is the same subject to receive the grown tissue. However, different subjects may receive the vascularized tissue if compatible to the first mentioned recipient.

The present invention is particularly directed to warm blood animals such as mammals including humans and other primates (e.g. gorillas, monkeys, orangutans, marmosets), livestock animals (e.g. sheep, cows, pigs, horses, donkeys, goats), laboratory test animals (e.g. mice, rats, hamsters, guinea pigs) and companion animals (e.g. dogs, cats).

In a particularly preferred embodiment, the donor subject and recipient are human and even more preferably, the same human subject.

The person skilled in the art will appreciate that a "vascular pedicle" is an artificial or naturally occurring arrangement of blood vessels or vessel replacements that comprises an artery taking blood to the site of the construct and a vein carrying it away. As mentioned above, the term "vascular pedicle" as used in the context of the present invention further comprises cells of other tissue or extracts or components thereof such as, for example, vascularized fat or adipose tissue attached or otherwise associated with the pedicle. In an alternative, a tissue extract or a recombinant, synthetic or purified component of the tissue is associated with the vascular pedicle.

Figure 1:
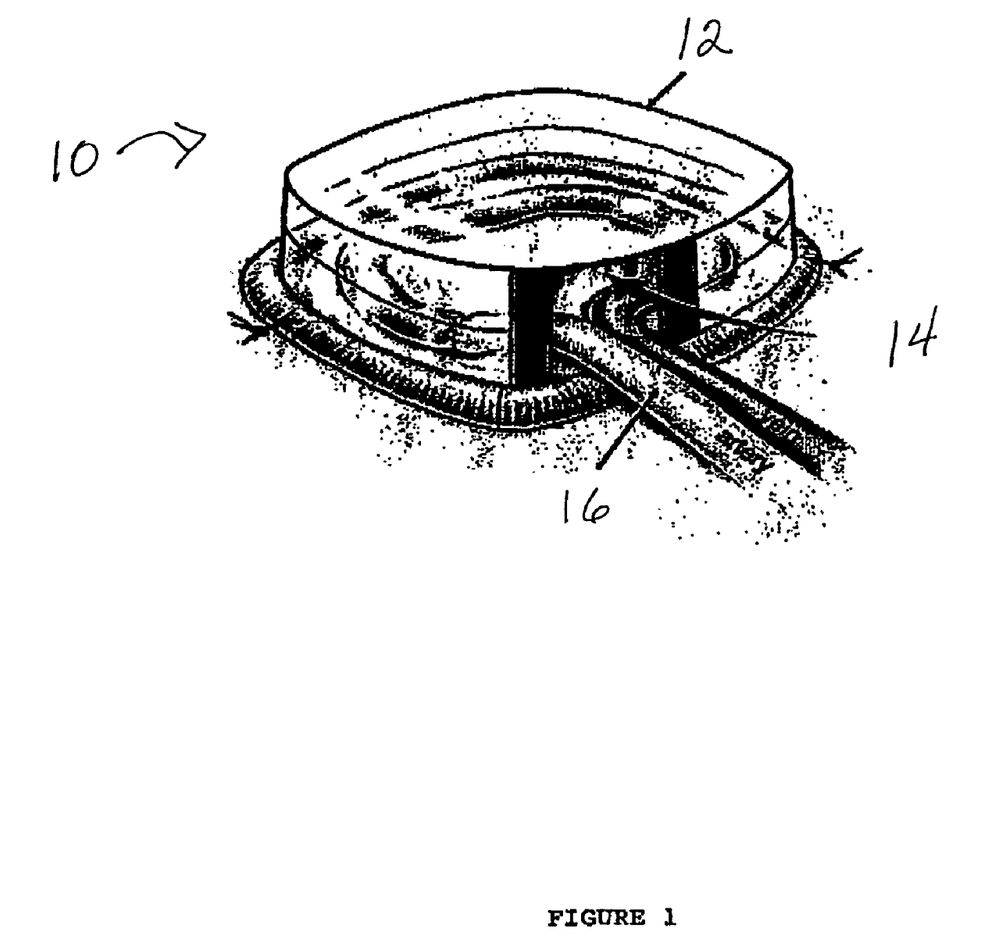
Figure 3:
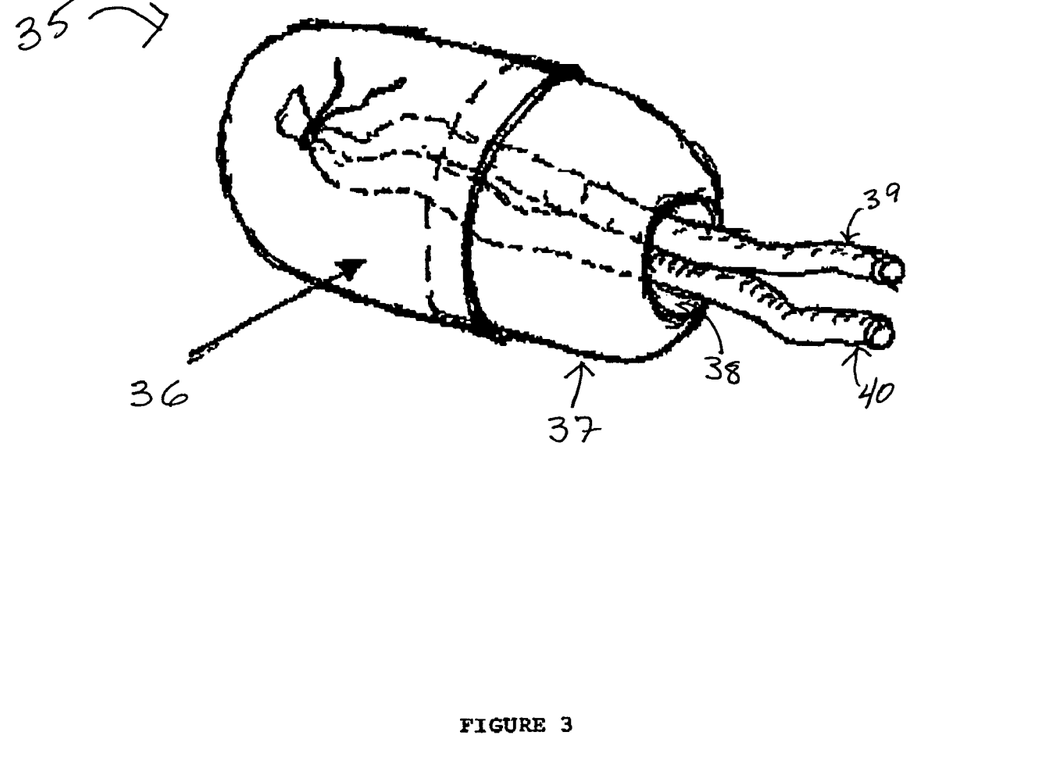
Figure 4A:
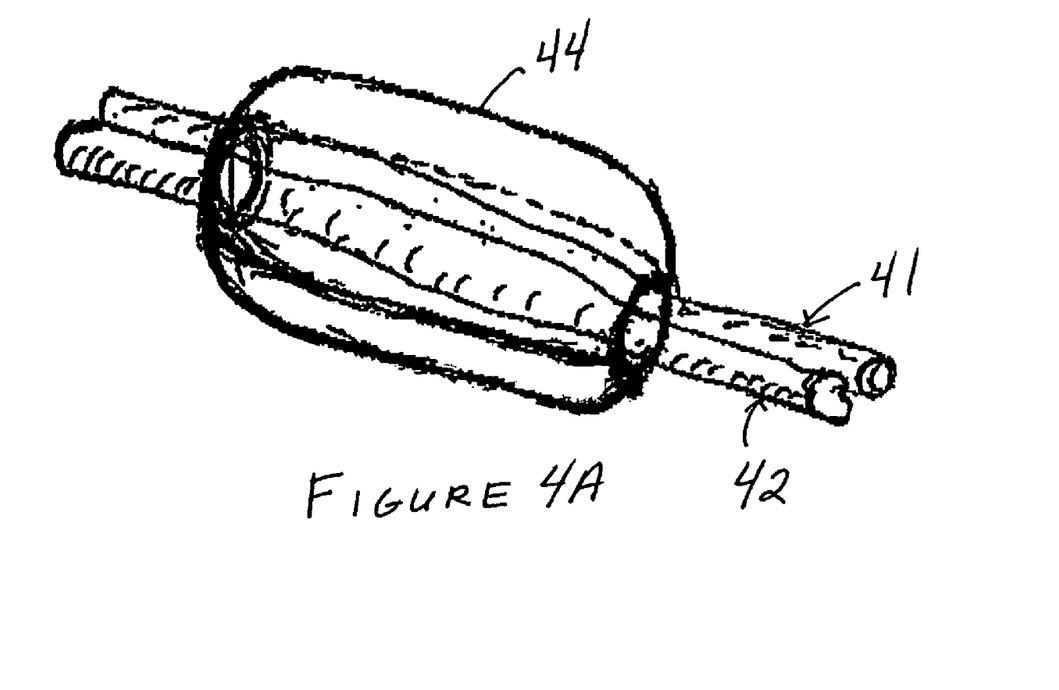
FIGS. 4A and 4B are diagrammatic representations showing two variants of a model chamber similar to that in FIG. 3 but with exit holes for the blood vessels at either end of the chamber. This allows an undivided, dissected length of blood vessels, placed side-by-side and in some variants, surrounded with extracellular matrix to form new tissue.
Figure 4B:
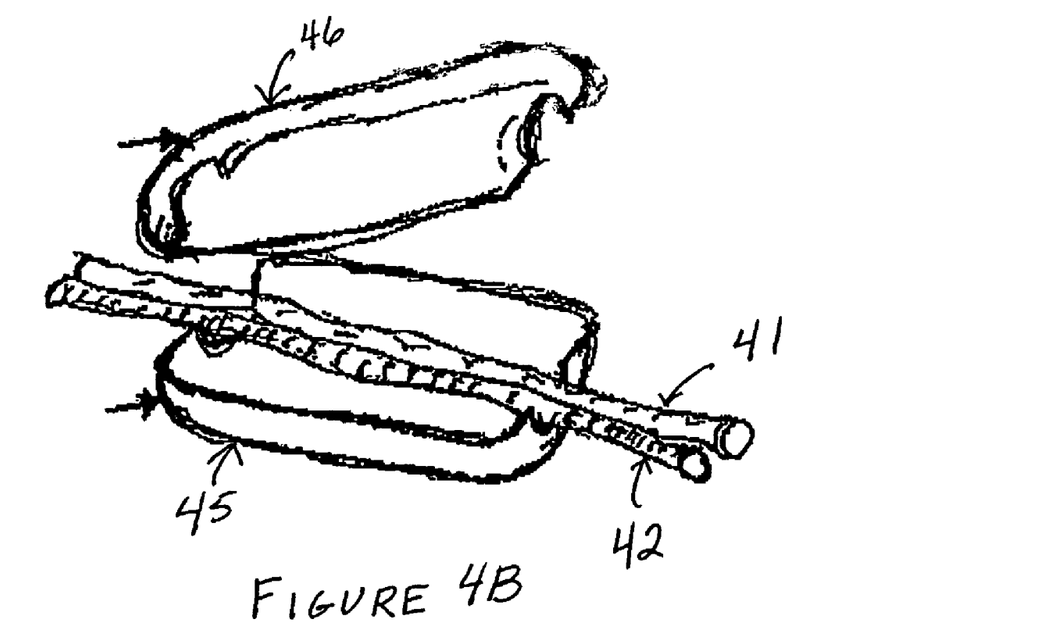

Preferably, the vascular pedicle comprises an AV loop or shunt. In an AV loop or shunt, the artery is either joined directly to the vein or connected via a graft of a similar diameter so that there is no impediment to blood flow (for example, as illustrated in FIG. 1). In one alternative arrangement, the artery and vein are both ligated and blood flow is via microscopic connections between the two (for example, as illustrated in FIG. 3). In another alternative the artery and vein are in a "flow through" configuration with the blood vessels entering at one end of a semi-closed chamber and exiting at the opposite side (for example, as illustrated in FIG. 4). In essence, the vascular pedicle comprises a functional circulatory system.

The term "functional circulatory system" as used herein describes a circulation that has at least one of the following properties: the vessels making up the circulation are patent, the vessels are capable of sustaining blood or blood-substitute flowing through them, the vessels are capable of supplying nutrients and/or oxygen to nearby tissue and the vessels are capable of forming new blood vessels by budding.

Optionally, the chamber is supplied with added extracellular matrix, for example, matrix deposited by cells in situ, reconstituted basement membrane preparations such as MATRIGEL (trademark) or laminin (mouse origin), AMGEL (trademark), HUMATRIX (trademark), or laminin (all of human origin) with or without matrix metalloproteinase inhibitors, polylactic-polyglycolic acid variants (PLGA), fibrin or plasma glue (autologous or heterologous) with or without fibrinolysis inhibitors, or native collagen (autologous or heterologous) with or without collagenase inhibitors.

In a preferred embodiment, extracellular matrix-like polylactic-polyglycolic acid sponges, DEXON (trademark) sponges, or sea sponges are added to the chamber. Combinations of matrices, such as PLGA sponges coated with one or more other matrix-forming components such as fibrin, laminin, fibronectin, collagen, low molecular weight hyaluronan and vitronectin are other preferred options. Freeze dried segments of tissues such as muscle or organs such as liver may be used as sources of matrix and growth factors. Preferably, the segments of tissues or organs are taken from the same species as the donor subject, and most preferably taken from the donor individual.

In a particularly preferred embodiment of the present invention, the donor subject is the same individual as the recipient animal, i.e. the graft is autologous. Alternatively the donor subject may be an immunocompromised animal, such as an athymic mouse or pig and the recipient may then be a different individual, i.e. the graft is heterologous. Other permutations and combinations of these procedures may include the use of either autologous or immunocompromised blood vessels, cells, tissue segments or growth factors implanted back into either the original donor or a different recipient individual. Whether or not the "maturity" of the graft confers immunoprotection on a heterologous graft is another variant that can be tested using routine techniques.

The tissue or cells used in the chamber may be supplemented with additional growth factors selected from the group consisting of "homing" factors to attract stem cells from the circulation, exogenous growth factors such as α-Fibroblast Growth Factor (αFGF or αFGF-1), β-Fibroblast Growth Factor (βFGF-1 or βFGF-2), Platelet-Derived Growth Factor (PDGF), Vascular Endothelial Growth Factor (VEGF-A,B,C,D or E), Angiopoietin-1 and -2, Insulin-like Growth Factor (IGF-1), Bone Morphogenic Protein (BMP-2 and -7), Transforming Growth Factor-α and -β (TGF-α, TGF-β), Epidermal Growth Factor (EGF), Connective Tissue Growth Factor (CTGF), Hepatocyte Growth Factor (HGF), Human Growth Hormone (HGH), Keratinocyte Growth Factor (KGF), Tumor Necrosis Factor-α (TNF-α), Leukemia Inhibitory Factor (LIF), Nerve Growth Factor (NGF), Granulocyte Macrophage Colony Stimulating Factor (GM-CSF) and other factors such as 3-isobutyl-1-methylxanthine (IBMX), insulin, indomethacin, dexamethasone, hyaluronan hexasaccharide, the PPAR-γ ligand Troglitazone, nitric oxide, prostaglandin E1, transferrin, selenium, parathyroid hormone (PTH), parathyroid hormone related peptide (PTHrP), etc, many of which are promoters of angiogenesis or vasculogenesis. Antibodies, agonists or antagonists to some of these growth factors or inhibitors of the chemical mediators can also be used to influence the type of tissue formed and the rate of its formation. The person skilled in the art will readily be able to test which growth factor(s), anti-growth factor antibodies, or inhibitors, or combination thereof, are most suitable for any given situation.

The support matrix may be used with autologous or heterologous cells, such as myoblasts transfected with Myo-D to promote formation of the skeletal muscle phenotype, stem cells with appropriate differentiation factors, keratinocytes seeded to produce thin skin constructs for face and neck reconstruction, etc. Optionally, the chamber may also comprise isografted or autologous cells selected from the group consisting of myoblasts, fibroblasts, pre-adipocytes and adipocytes, cardiomyocytes, keratinocytes, endothelial cells, smooth muscle cells, chondrocytes, pericytes, bone marrow-derived stromal precursor cells, embryonic, mesenchymal or haematopoietic stem cells, Schwann cells and other cells of the peripheral and central nervous system, olfactory cells, hepatocytes and other liver cells, mesangial and other kidney cells, pancreatic islet β-cells and ductal cells, thyroid cells and cells of other endocrine organs.

Alternatively the support matrix may be used with additional autologous or isografted portions of skeletal or cardiac muscle, pancreas, liver, epididymal and other subcutaneous fat, nerves (peripheral, blood vessel-associated, etc), kidney, bowel, ovary, uterus, testis, olfactory tissue or glandular tissue from endocrine organs. The tissue encompasses any aggregates of cells, with or without additional extracellular material such as extracellular matrix, either taken directly from an animal or produced as a result of manipulation of cells in tissue culture, or a combination of the two. In other variants such tissue segments may be rendered ischaemic, cell-depleted or necrotic in order to provide cues or signals to the surviving stem cells and other cells which may influence tissue development.

Depending on the nature of the supplementation provided to the cells, the vascularized tissue is enabled to differentiate. In a particularly preferred embodiment, stem cells, together with appropriate extracellular matrix and growth factor supplements, are supplied to the support matrix in order to produce vascularized, differentiated tissues or organs. Suitable pluripotent stem cells can be derived from:
  blood;
  bone marrow;
  specific organs or tissues, including mesenchymal stem cells;
  cultured cells, which may be transfected or differentiated; or
  placental stem cell banks.

Sources such as bone marrow, ischaemic skeletal muscle and subcutaneous adipose tissue are preferred. Other potential sources of pluripotent stem cells are blood, especially from a fetus or newborn individual but also from an adult, and human placenta. A number of stem cell banks such as bone marrow or cord blood banks are already established. Human embryos are a potential clinical source of stem cells.

The type of differentiated cells produced depends on the origin of the stem cells, the local environment, the presence of tissue-specific growth or differentiation factors, and other factors. For example, ischaemic skeletal muscle placed in the chamber with an AV loop or shunt differentiates into predominantly adipose tissue after 2-10 weeks. Without wishing to be limited by any proposed mechanism, in this case, mesenchymal stem cells in the muscle, together with the stimulus of acidic ischaemic metabolites, may potentially be responsible for this differentiation. One advantage of using stem cells is their huge proliferative capacity, so that relatively few cells are required to generate a large colony for seeding the chamber and the AV loop or shunt.

Preferably, the vascular pedicle, such as an AV loop or shunt, with attached tissue, such as fat or adipose tissue or extract or components thereof, comprises an artery joined to a venous graft, which is in turn joined to a vein. Alternatively the AV loop or shunt comprises an artery joined to a vein directly, or the AV loop or shunt comprises an artery joined sequentially to a venous graft, an arterial graft and a vein. In another variant, which is useful where microsurgical anastomosis of vessels is technically difficult or impossible, a pedicle comprising the ligated stumps of an artery and vein (e.g. the femoral vein) placed side-by-side in the chamber is used as the blood vessel supply. In another preferred embodiment of the present invention, the AV loop or shunt vessels flow in and out of the chamber from the same edge. In another variant, the artery and vein are neither divided nor formed into a shunt but instead flow in one side of the chamber and out the opposite side (see, for example, FIG. 4). In yet another variant suitable for extremely small blood vessels, the artery and vein are divided and placed side by side in the chamber, the vessels both entering from the same edge; this is illustrated in FIG. 3.

The graft portion of the AV loop or shunt may be derived from the host or from a separate donor. Cold-stored or pre-fabricated vessels may also be used.

In one preferred embodiment of the present invention, an additional step involves the incorporation of a nerve stump, so that tissue in or around the support matrix may become innervated. Skeletal muscle, for example, requires proximity to a nerve for its maintenance and maturity; otherwise it will atrophy.

Preferably, the support matrix, such as a fabricated chamber containing the vascular pedicle and attached tissue, such as fat, adipose tissue or extract or components thereof, has a defined internal and/or external dimensions. The internal and/or external dimensions, volume, and shape may be varied in order to influence the volume and shape of the new tissue being produced. For example:
  the internal volume of the chamber may be increased, without altering the external size of the chamber, by providing thinner walls;
  the shape of the chamber may be constructed to resemble that of the target organ or body part, such as an ear, nose, breast, pancreas, liver, kidney, finger or other joint;
  the degree of permeability of the walls of the chamber may be varied; for example the chamber may include a semi-permeable membrane component to allow selective perfusion of molecules into and out of the chamber, or a plurality of perforations may be placed in the walls of the chamber to allow an increased flow of metabolites and metabolic by-products, growth factors and other factors that influence cell survival, growth and differentiation between the inside and outside of the chamber; the size, shape and number of the perforations may be selected according to the size of the donor vascularized tissue and the requirement to keep the contents of the chamber isolated from direct contact with the implantation site; alternatively, a semi-permeable component may be placed within the chamber in order to isolate "feeder" cells from immune reactions.

As an example of the latter, populations of fibroblasts or other cells can be transfected, then used as a source of the transfected gene product(s) within the chamber. This construct is placed within a semi-permeable pocket out of contact with the host's immune system. Drug delivery is used to switch the transfected gene on or off. These cells survive by diffusion as long as they receive adequate nutrients but will eventually die.

The surface chemistry of the support matrix may be modified in order to modify the interaction between the tissue and the matrix to provide a stimulus for differentiation or to incorporate or be coated with a gel, such as alginate, which mediates the slow release of a chemical or biological agent to create a gradient.

The degree of internal support within the support matrix may be varied, e.g. there may be:
  no support;
  a solid support which directs, encourages or inhibits the growth of the new tissue, or excludes new tissue, or is incorporated into the new tissue;
  a transient support based on resorbable materials;
  a porous supporting material which supports cell and vascular ingrowth, providing a skeleton over which the new tissue can be generated, e.g. sponge-like materials such as blown PTFE materials, PLGA sponges of variable composition and porosity, etc; or
  a support formed from materials which direct tissue differentiation, such as hydroxyapatite or demineralized, granulated bone.

Preferably, the exterior surface of the chamber bears a means by which the chamber may be attached and/or immobilized to the desired region of the body.

Accordingly, another aspect of the present invention provides a vascularized tissue, comprising differentiated tissue with a vascular supply, suitable for use as a graft in tissue transplantation and/or tissue repair or augmentation or regeneration.

Preferably, the graft predominantly comprises tissue selected from the group consisting of adipose tissue, cartilage, bone, skeletal muscle, cardiac muscle, loose connective tissue, ligament, tendon, kidney, liver, neural tissue, bowel, endocrine and glandular tissue. More preferably, the graft predominantly comprises vascularized adipose tissue, skeletal muscle, cartilage or bone tissue or tissue comprising pancreatic islet and/or ductal cells, kidney cells or liver cells.

A further aspect of the present invention contemplates a method of repairing a tissue deficit, said method comprising generating vascularized tissue by creating a vascular pedicle comprising a functional circulatory system and having tissue or tissue extract or a component thereof impregnated, attached or otherwise associated with the vascular pedicle; associating the vascular pedicle within and/or on a support matrix; optionally seeding the support matrix with isolated cells or pieces of tissue; implanting the support matrix containing the vascular pedicle into a recipient at a site where the functional circulatory system can be anastomosized to a local vein or artery; and leaving the support matrix at the implantation site for a period sufficient to allow the growth of vascularized new tissue and then removing the vascularized tissue having the desired size, vascularity and degree of differentiation and transferring the generated tissue with or without the support matrix to the site of tissue deficit in the same or compatible recipient.

The term "tissue deficit" includes a shortfall in the normal volume, structure or function of a tissue in the recipient. Such a tissue may be selected from, but is not limited to, superficial tissues such as skin and/or underlying fat, muscle, cartilage, bone or other structural or supporting elements of the body, or all or part of an organ. The augmentation of otherwise normal tissues for cosmetic purposes, such as forms of breast augmentation, is also provided by the present invention. A person skilled in the art will readily recognize that such a tissue deficit may be a result of trauma, surgical or other therapeutic intervention, or may be congenitally acquired.

The ability to repair a tissue deficit and/or augment or regenerate inappropriately depleted tissue, using the means outlined above, provides the further possibility of facilitating the delivery of one or more desirable gene product(s) to a subject. Cells and/or developing tissue within or around the support matrix may be transformed with an appropriate genetic construct, comprising the desired gene, prior to being transplanted into the recipient subject.

Accordingly, yet another aspect of the invention provides a method of providing a subject with a gene product, said method comprising generating vascularized tissue capable of expressing a genetic construct wherein said vascularized tissue is generated by a vascular pedicle comprising a functional circulatory system and having tissue or tissue extract or a component thereof impregnated, attached or otherwise associated with the vascular pedicle; associating the vascular pedicle within and/or on a support matrix; seeding the support matrix with isolated cells or pieces of tissue carrying said genetic construct; implanting the support matrix containing the vascular pedicle into a recipient at a site where the functional circulatory system can be anastomosized to a local vein or artery; leaving the support matrix at the implantation site for a period sufficient to allow the growth of vascularized new tissue expressing or carrying said genetic construct and then transplanting the vascularized tissue to the desired site in the same or a compatible recipient.

The timing of the genetic transformation of the tissue-producing cells can be varied to suit the circumstances, for example, the cells may be transformed at the time of setting up the chamber construct, during the incubation, or immediately prior to transplantation.

In addition, the vascularized tissue may also be subject to transformation of genetic construct.

The provision of gene products can take several forms. One example is the transfection of myoblasts with the Myo-D gene to create tissue with a normal skeletal muscle phenotype. Such transfected cells may then be seeded into the desired chamber, matrix and AV loop or shunt to generate vascularized skeletal muscle. This may have implications for the treatment of muscular dystrophy and other genetically inherited muscle diseases. A second example is the transfection of pancreatic islet cells with a "healthy" phenotype and their seeding into the chamber. This approach may prove to be useful in the treatment of diabetic patients. In a third example, cells are transfected with a growth factor gene or an angiogenesis-promoting gene, such as PDGF, βFGF or VEGF, prior to seeding them into the chamber together with the AV loop or shunt and selected matrix. This continuous production of growth factor is designed to speed up the rate of development of and the rate of new blood vessel formation within the new tissue/organ. A "gene product" includes a peptide, polypeptide or protein, mRNA, RNA, RNAi or siRNA.

Preferably, the genetic construct is a DNA or RNA vector which encodes an expression product or which is used to generate a knock-in or knock-out mutation. Conveniently, the genetic construct comprises a selectable marker. A selectable marker in the vector allows for selection of targeted cells that have stably incorporated the genetic construct. This is especially useful when employing relatively low efficiency transformation techniques such as electroporation, calcium phosphate precipitation and liposome fusion where typically fewer than 1 in 1000 cells will have stably incorporated the exogenous DNA or RNA. Using high efficiency methods, such as microinjection into nuclei, typically from 5-25% of the cells will have incorporated the targeting DNA or RNA; and it is, therefore, feasible to screen the targeted cells directly without the necessity of first selecting for stable integration of a selectable marker. Either isogenic or non-isogenic DNA or RNA may be employed.

Examples of selectable markers include genes conferring resistance to compounds such as antibiotics, genes conferring the ability to grow on selected substrates, genes encoding proteins that produce detectable signals such as luminescence. A wide variety of such markers are known and available, including, for example, antibiotic resistance genes such as the neomycin resistance gene (neo) and the hygromycin resistance gene (hyg). Selectable markers also include genes conferring the ability to grow on certain media substrates such as the tk gene (thymidine kinase) or the hprt gene (hypoxanthine phosphoribosyltransferase) which confer the ability to grow on HAT medium (hypoxanthine, aminopterin and thymidine); and the bacterial gpt gene (guanine/xanthine phosphoribosyltransferase) which allows growth on MAX medium (mycophenolic acid, adenine and xanthine). Other selectable markers for use in mammalian cells and plasmids carrying a variety of selectable markers are described in Sambrook et al., *Molecular Cloning—A Laboratory Manual*, Cold Spring Harbour, N.Y., USA, 1990.

The preferred location of the marker gene in the genetic construct will depend on the aim of the gene targeting. For example, if the aim is to disrupt target gene expression, then the selectable marker can be cloned into targeting DNA corresponding to coding sequence in the target DNA. Alternatively, if the aim is to express an altered product from the target gene, such as a protein with an amino acid substitution, then the coding sequence can be modified to code for the substitution, and the selectable marker can be placed outside of the coding region, for example, in a nearby intron.

The selectable marker may depend on its own promoter for expression and the marker gene may be derived from a very different organism than the organism being targeted (e.g. prokaryotic marker genes used in targeting mammalian cells). However, it is preferable to replace the original promoter with transcriptional machinery known to function in the recipient cells. A large number of transcriptional initiation regions are available for such purposes including, for example, metallothionein promoters, thymidine kinase promoters, β-actin promoters, immunoglobulin promoters, SV40 promoters and human cytomegalovirus promoters. A widely used example is the pSV2-neo plasmid which has the bacterial neomycin phosphotransferase gene under control of the SV40 early promoter and confers in mammalian cells resistance to G418 (an antibiotic related to neomycin). A number of other variations may be employed to enhance expression of the selectable markers in animal cells, such as the addition of a poly(A) sequence and the addition of synthetic translation initiation sequences. Both constitutive and inducible promoters may be used.

The present invention further provides a model system for vascularized tissue comprising a support matrix comprising a vascular pedicle and having tissue or extract or component thereof attached thereto and optionally an extracellular matrix operably connected to an extracorporeal circulation apparatus and renal dialysis filter.

The extracorporeal circulation apparatus and renal dialysis filter may be of any suitable conventional type. The cells forming the tissue in the chamber are optionally transformed so as to express a heterologous gene. This model system may be used for culturing, recruiting, growing and studying the behavior of stem cells or tissue containing precursor cells, either in vitro or in vivo. Because of the ability to alter the environment of the chamber with added growth, differentiation and chemical factors, it is possible to produce a wide variety of tissues and organs by this process.

The ability to generate autologous vascularized tissue of a defined composition and at any anatomical site in the body where it is possible to create an AV loop or shunt or suitable vascular pedicle has many other applications. At its localized site, the tissue in the fabricated chamber may, for example, be manipulated by:
  gene transfection;
  administration a local drug or other "factor", or
  creating a site of circulatory stem cell homing.

Furthermore, the tissue and exudate in the chamber may readily be harvested to monitor progress of tissue growth and development.

The present invention further provides a support matrix suitable for use in generating vascularized tissue. Generally, the support matrix is adapted to receive a vascularized pedicle comprising a functional circulatory system and tissue or tissue extract or component thereof attached or associated therewith. The support matrix is preferably in the form of a fabricated chamber. The support matrix may also be packaged for sale with instructions for use. The present invention provides, therefore, a medical device comprising a support matrix adapted to receive a vascular pedicle comprising a functional circulatory system and tissue or tissue extract or component thereof attached or associated therewith, the device optionally packaged for sale with instructions for use.

In one embodiment, the support matrix is a fabricated chamber having an internal and external portion wherein the internal and/or external portion is adopted to receive a vascular pedicle comprising a functional circulatory system and tissue or tissue extract or component thereof attached or associated therewith.

The present invention is further described by the following non-limiting Examples.

Example 1

Preparation of Support Matrix

A custom-made polycarbonate chamber is prepared. It comprises a top and a bottom, and when the two halves are sealed together the internal volume is 0.45-0.50 mL. The general construction of the chamber 10 is illustrated in FIG. 1. In this exemplary chamber, the chamber is a transparent plastic cylindrical chamber with lid 12.

The basic chamber for use in rats is made of polycarbonate. In one variant, the chamber is made of polylactic acid or PLGA. The chamber is in the shape of a cylinder of external dimensions 14 mm diameter and 4 mm high, with a saw cut on one side to create an opening for the blood vessel entry and exit. Another variant has cut openings on opposite sides of the chamber to allow blood vessels to flow in one side and out the other. The chamber has a base and a removable lid 12. The base has holes to allow anchoring of the chamber to subcutaneous tissue. The internal volume is approximately 0.45-0.50 mL. The internal volume of this basic chamber can be varied, maintaining the same external volume, by using thinner walls, which may even be as thin as a standard plastic film used in food storage. The chamber 10 also has at least one hole 14 for insertion of the arteriovenous loop fistula 16.

Figure 2:
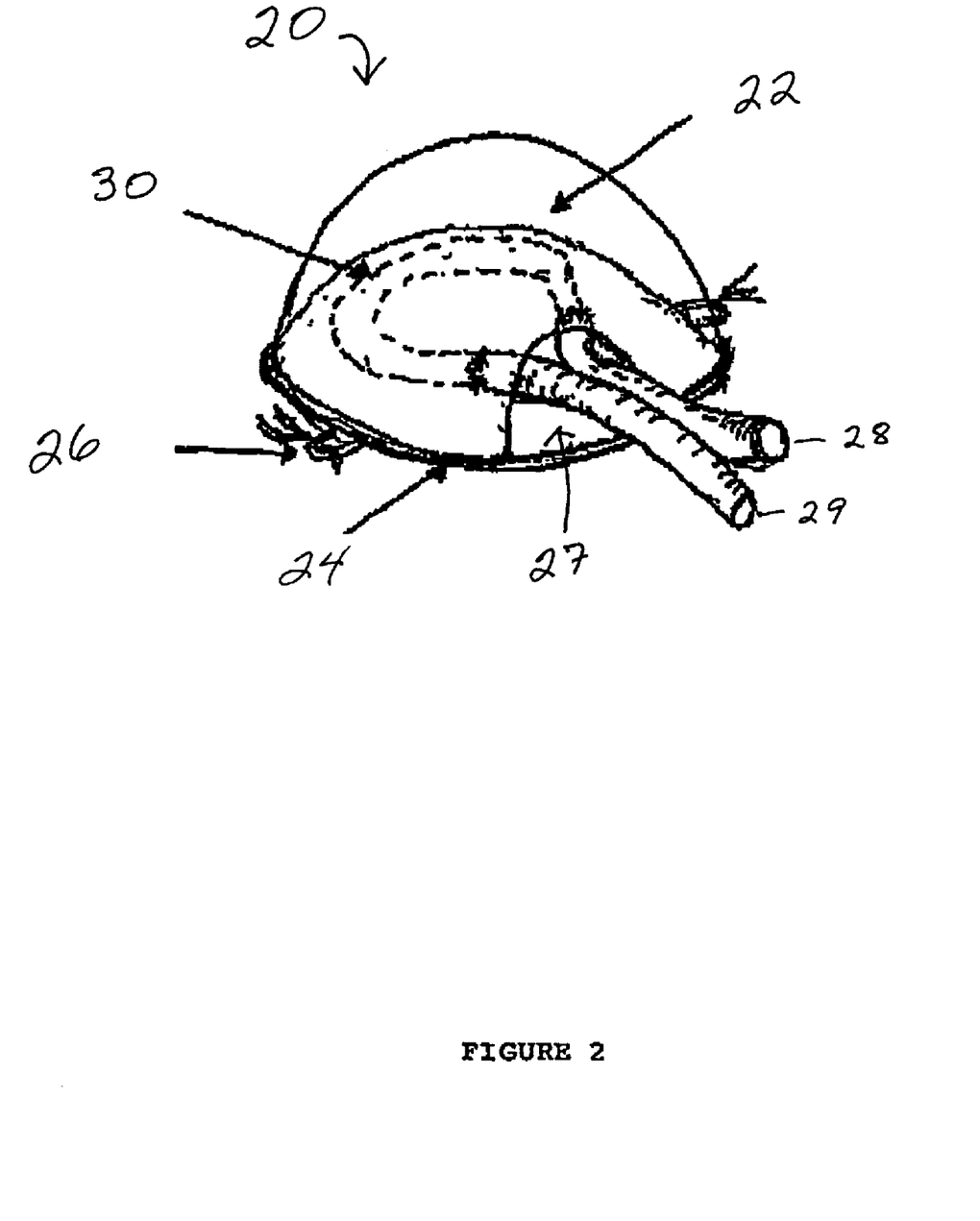
FIG. 2 is a diagrammatic representation showing a configuration similar to FIG. 1 except that the lid of the chamber is dome-shaped and the edges of the chamber are more rounded to minimize wound breakdown.

An alternative design 20 is in the shape of a "dome" with more rounded edges, as shown in FIG. 2. In this alternative, the chamber has a dome cap 22 that attaches to a base plate 24. The base plate has a flange 26 for fixation to bed. This alternative also has a hole 27 through which the artery 28 and vein 29 can be inserted to form the vessel loop under the dome cap 22.

Another embodiment is in the form of an elongated, flattened cigar shape 35 as shown in FIG. 3. In this embodiment, there is a capsule 36 sleeving over a mated part 37. As shown, the hole 38 for the artery 39 and vein 40 is in the mated part 37. The flattened cigar shape embodiment 35 fits readily into the subcutaneous space in the groin. For the purposes of specific grafts, the shape of the chamber may be designed to mimic the shape or contours of a particular body part, for example a human finger joint or thumb, human ear, human nose, human breast, etc.

Yet another design is illustrated in FIGS. 4A and 4B. In this design, the artery 41 and vein 42 are neither divided nor formed into a shunt but instead flow in one side of the chamber and out the opposite side. Thus, in the embodiment of FIG. 4A a unitary chamber 44 is provided with a hole on either end to facilitate entry and exit of the artery 41 and vein 42. In the variant of this design illustrated in FIG. 4B, the chamber is comprised of a base 45 and a removable lid 46.

Thus, it can be seen that any of a number of different variants can be designed for use in a wide variety of different circumstances.

In this regard, the size of the chamber may scaled up or down to suit the size of the host. Hence, the internal volume for a chamber to be used in a mouse may be approximately 0.1-0.2 mL, in a rabbit 10-12 mL, but in a human can be up to approximately 100-200 mL.

The chamber may optionally be sealed. In the standard version, the opening allows limited contact with the surrounding tissue and total uninterrupted contact with the blood supply. In a sealed variant, the opening is engineered to allow just enough space for the ingoing artery and outflowing vein without crushing the blood vessels. The vessel ports are sealed, for example with fibrin glue, to avoid contact of the developing graft with surrounding tissue.

The surface of the polycarbonate chamber can be left in its native hydrophobic state or can be rendered relatively more hydrophilic by the use of polylactic acid or the pre-treatment of polycarbonate with a thin film of poly-L-lysine. In one useful configuration, the surface of the chamber comprises a plurality of perforations, allowing increased contact with growth factors in the surrounding tissue. The size and shape of the perforations may be tailored to optimise the passage of the desired factors, while minimizing or preventing the passage of cells.

If the chambers are made of glass or Pyrex they can be coated with silicone.

The chamber design should ideally fit comfortably into the recipient site and should be of a rounded shape and of a sufficiently small size to avoid wound break down.

The internal contents of the chamber are sufficiently large to accommodate an osmotic pump (e.g. an ALZET [trademark] osmotic mini pump) to deliver drugs, growth factors, antibodies, inhibitors or other chemicals at a controlled rate. In one alternative method of drug/factor delivery, the osmotic pump may be placed subcutaneously outside the chamber with a plastic tube leading from the pump placed inside the chamber, e.g. at the centre of the AV loop.

Example 2

Creation of an AV Shunt Loop Inside the Tissue Chamber

The basic model has been described by Tanaka et al., 1996, supra. Briefly, male Sprague-Dawley rats (225-285 g) are anaesthetized with intraperitoneal phenobarbitone (50 mg/kg; 2.5 mL of a 6 mg/mL solution). Under sterile conditions an inferior-based flap is created in the right groin to expose the femoral vessels from the inguinal ligament to the superficial epigastric branch. A longitudinal incision was made in the left groin to harvest the left femoral vein from inguinal ligament to the superficial epigastric branch. This vein graft (approximately 1.5-3 cm long; usually 2 cm) was interposed between the recipient right femoral vein and artery at the level of the superficial epigastric artery by microsurgical techniques using 10-0 sutures. The shunt is placed into the chamber, the lid closed and the construct sutured to the groin musculature with the aid of small holes on the base of the chamber. An adipose layer was placed over the chamber and the wound closed with 4-0 silk sutures.

The growth chambers with the AV shunts are harvested at either two, four or 12 weeks post implantation.

Example 3

Assessment of Vascularization and Tissue Creation

At the specified time of exploration, the chamber is opened and the vessels cleaned and tested for patency. The vessels are tied off with a 5-0 silk suture at the entrance of the chamber and the flap harvested. In two of the five rats in each group, the flap is perfused via the aorta with India ink prior to harvest (details below). The flaps are assessed for volume and weight and placed in buffered 10% v/v formal saline (BFS) for histological examination. The animals are sacrificed with an intracardiac dose of sodium pentabarbitone (~3 ml of 250 mg/m: solution) at the completion of the exploration.

Example 4

Tissue Mass and Volume

The tissue in the chamber is removed and its wet weight and volume recorded. The volume of the tissue is assessed by a standard water displacement technique. The tissue is suspended by a 5-0 silk suture in a container of normal saline which had been zeroed previously on a digital balance. Care was taken not to touch the container with the specimen. The weight recorded is the volume of the tissue specimen (with a density equal to that of normal saline, 1.00 g/mL). The mass of the specimen is assessed at the same time on the same digital scale by allowing the tissue to rest on the base of the container, and recording the weight.

Example 5

India Ink Perfusion

In order to perfuse the flaps with India ink, the abdomen is opened via a midline incision. The intestines are gently retracted to the periphery and the periaortic fat stripped away. The proximal aorta and inferior vena cava is ligated. The aorta is cannulated with a 22-gauge angiocatheter which was secured with a distal suture around the angiocatheter and aorta. A venotomy is carried out in the inferior vena cava. The aorta is perfused with 10 mL of heparinised saline to flush out the retained blood, the animal was sacrificed with intracardiac sodium pentabarbitone (3 mL of a 250 mg/mL solution), the aorta infused with 3 mL buffered 10% v/v formol saline (BFS) and then with 5 mL India ink in 10% v/v gelatin. The flap vessels are then tied off. Tissue from the chamber is removed, fixed in BFS, cleared in cedar wood oil and the pattern of vessels visualized microscopically using transmitted light and image analysis (VIDEO PRO™ imaging).

Example 6

Histology

Specimens are fixed in buffered formol saline and embedded in paraffin. Sections (5 μm) are cut and stained with either haematoxylin & eosin (H & E) or Masson's Trichrome.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Erol and Spira, *Surgery* 66: 109-115, 1980
Khouri et al., *Surgery* 114: 374-380,1993
Tanaka et al., *Jpn. PRS* 16: 679-686, 1996

What is claimed is:

1. A method of growing vascularized adipose tissue to a size and shape that stimulates a volume or structure of a tissue to be augmented at a desired site in a donor subject, comprising:
    a) creating a functional circulation on a vascular pedicle comprising fat or adipose tissue attached thereto in a donor subject;
    b) enclosing the vascular pedicle within a fabricated chamber, the chamber having internal dimensions which are of said size and shape, wherein the chamber is filled with added reconstituted basement membrane preparation;
    c) implanting the chamber containing the vascular pedicle into the donor subject at a site where such an anatomical construct can be created; and
    d) leaving the chamber in the implantation site for a period sufficient that donor vascularized adipose tissue grows to the size and shape of the chamber, wherein the donor vascularized adipose tissue is viable for transfer to the desired site.

2. The method of claim 1, further comprising transferring the donor vascularized adipose tissue to a desired site of a recipient, thereby augmenting the volume or structure of tissue at the desired site of the recipient.

3. The method of claim 2, further comprising anastomosing blood vessels of the donor vascularized adipose tissue to an artery and vein at said desired site.

4. The method of claim 1, wherein the reconstituted basement membrane preparation comprises MATRIGEL™ preparation.

\* \* \* \* \*